US006580003B2

(12) United States Patent
Deng et al.

(10) Patent No.: US 6,580,003 B2
(45) Date of Patent: Jun. 17, 2003

(54) CATALYTIC ASYMMETRIC DESYMMETRIZATION OF MESO COMPOUNDS

(75) Inventors: Li Deng, Waltham, MA (US); Yonggang Chen, Waltham, MA (US); Shikai Tian, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 09/825,167

(22) Filed: Apr. 3, 2001

(65) Prior Publication Data

US 2002/0038048 A1 Mar. 28, 2002

Related U.S. Application Data

(60) Provisional application No. 60/194,520, filed on Apr. 4, 2000.

(51) Int. Cl.[7] .......................... C07C 67/00
(52) U.S. Cl. .......................... 560/127; 560/192; 560/204
(58) Field of Search .......................... 560/192, 204, 560/127; 562/590; 544/351

(56) References Cited

U.S. PATENT DOCUMENTS 2,566,957 A * 9/1951 Pedlow et al. .............. 428/420

FOREIGN PATENT DOCUMENTS

GB 1045091 10/1966

OTHER PUBLICATIONS

John D. Roberts and Marjorie C. Caserio, "Basic Principles of Organic Chemistry", Benjamin, New York, 1964, p. 288 & 289.*

Grant, R.L. and Grant, Claire, "Grant & Hackh's Chemical Dictionary, 5th Ed.", 1990, McGraw–Hill, New York, pp. 558–559.*

Hawley, Gessner, "The Condensed Chemical Dictionary", 1977, Van Nostrand, New York, p. 823.*

Aldrich Chemical Company, 1992, p. 1165, item #13,689–1.*

Hawley, Gessner, "The Condensed Chemical Dictonary", 1977, Van Nostrand, New York, p. 626.*

Kolasa, T. et al, Tet., 45, 1989, 3071–3080.*

Aitken et al.; "Catalytic asymmetric Synthesis of Highly Functionalised Compounds With Six Contiguous Stereocentre", J. Chem. Soc. Chem. Commun, pp. 632–634, (1988).

Becker and Sharpless; "A New Ligand Class for the Asymmetric Dihydroxylation of Olefin", Angew Chem. Int. Ed. Engl., 35(4):448–450, (1996).

International Search Report Completed on Nov. 9, 2001 and Mailed on Nov. 22, 2001.

Hiratake et al.; "Catalytic Asymmetric Induction from ProchiralnCyclic Acid Anhydrides Using Cinchona Alkaloids", J. Chem. Soc., Chem. Commun. pp. 1717–1719, (1985).

Seebach et al.; "Highly Enantioselective Opening of Cyclic meso–Anhydrides to Isopropyl Hemiesters With Diisopropoxytitanium TADDOLates", Angew. Chem. Int. Ed. Engl. 34(21): 2395–2396, (1995).

Bolm et al.; "Simple and Highly Enantioselective Noenzymatic Ring Opening of Cyclic Prochiral Anhydrides", Synlett, No. 2 : 195–196, (1999).

(List continued on next page.)

*Primary Examiner*—John M. Ford
*Assistant Examiner*—Thomas McKenzie
(74) *Attorney, Agent, or Firm*—Dana M. Gordon; Foley Hoag LLP

(57) ABSTRACT

The present invention relates to methods for the synthesis of chiral non-racemic products, e.g., enantiomerically-enriched hemiesters, from prochiral starting materials, e.g., meso anhydrides. The present invention also relates to catalysts for the aforementioned methods, and methods for synthesizing these catalysts.

14 Claims, 10 Drawing Sheets

*meso* cyclic anhydride
(DHQD)$_2$AQN, MeOH
chiral non-racemic product
60-95% yield

| Entry | Anhydride | Catalyst Loading (mole %) | Solvent | Temp. (°C) | ee (%)[c] | Product[b] |
|---|---|---|---|---|---|---|
| 1 |  | 5 | Ether | -20 | 98 (98) |  |
| 2 |  | 30 | Ether | -35 | 91 (82) |  |
| 3 |  | 30 | Ether | -35 | 90 (83) |  b |
| 4 |  | 10 | Toluene | r.t. | 76[a] |  | a: (DHQD)$_2$PHAL was used as catalyst. b: the absolute configuration was determined by comparison with authentic samples prepared by known procedure. c: the ee was determined by chiral GC or following a literature procedure. Enantiomeric excesses in parentheses were obtained using (DHQ)$_2$AQN as catalyst; the products obtained in these cases were of the opposite absolute configurations.

OTHER PUBLICATIONS

Couché et al.; "The Synthesis of Highly Functionalized Enantiometrically Enriched Cyclohexanes. An Approach to Carba–Sugars and Aminocarba–Sugars." Synlett, No. 1: 87–89, (1999).

Hecker and Heathcock,; "Total Synthesis of (+)–Dihydromevinolin", J. Am. Chem. Soc. 108: 4586–4594, (1986).

Rosen and Heathcock,; "Total Synthesis of (+)–Compactin", J. Am. Chem. 107: 3731–3733, (1985).

Heathcock et al.; "Total Synthesis and Biological Evaluation of Structural analogues of Compactin and Dihydromevinolin", J. Med. Chem. 30: 1858–1873, (1987).

Hiratake et al.; "Enantiotopic–Group Differentiation. Catalytic Asymmetric Ring–Opening of Prochiral Cyclic Acid Anhydrides with Methanol, Using Cinchona Alkaloids", J. chem. Soc. Perkin Trans. 1: 1053–1058, (1987).

Jaeschke and Seebach,; "Highly Enantioselective Ring Opening of Cyclic Meso–Anhydrides to Isopropyl Hemiesters with Ti–TADDOlates: an alternative to Hydrolytic Enzymes?", J. Org. Chem. 63: 1190–1197, ( 1998).

Albers et al.; "Desymmetrisation of meso–Anhydrides Utilising (S)–Proline Derivatives", Synthesis, pp. 393–398, (Mar. 1996).

Theisen et al.; "Prochiral Recognition in the Reaction of 3–Substituted Glutaric Anhydrides with Chiral Secondary Alcohols", J. Org. Chem. 58: 142–146, (1993).

Shimizu et al.; "Enantioselective Esterification of Cyclic Discarboxylic Anhydrides Using Chiral Aminol Alcohols as Auxiliaries", Bull. Chem. Soc. Jpn 66(7): 2128–2130, ( 1993).

Aitken et al.; "Catalytic Asymmetric Synthesis of Highly Functionalised Compounds with Six Contiguous Stereocentres", J. Chem. Soc. Chem. Commun. pp. 632–634, (1988).

Aitken and Gopal, "Catalytic Asymmetric Ring–openning of Bridged Tricyclic Anhydrides", Tetrahedron Asymmetry 1(8): 517–520, ( 1990).

Konoike and Araki, "Practical Synthesis of Chiral Synthons for the Preparation of HMG–CoA Reductase Inhibitors", J. Org. Chem. 59: 7849–7854( 1994).

Ohtani et al.; "Highly Effective and Practical Enantioselective Synthesis of Half–Esters of Bicyclo[2.2.1]heptanedicarboxylic Acid", J. Org. Chem. 56: 4120–4123 (1991).

Evans et al; "$C_2$–Symmetric Cu(I I) Complexes as Chiral Lewis Acids. Catalytic Enantioselective Michael Addition of silylketene Acetals to Alkylidene Malonates", J. Am. Chem. Soc. 121: 1994–1995, ( 1999).

Ohtani et al.; "Enantioselective Synthesis of S–1452, an Orally Active Potent Thromboxane $A_2$ Receptor Antagonist", J. Org. Chem. 56: 2122–2127, ( 1991).

Borzilleri and Weinreb; "Total Synthesis of Popuamine via a Stereospecific Intramolecular Imino Ene Reaction of an Allenylsilane", J. Am. Chem. Soc., 116: 9789–9790, (1994).

Borzilleri et al; "Total Synthesis of the Unusual Marine Alkaloid (– )– Papuamine Utilizing a Novel Ene Reaction", J. Am. Chem. Soc. 117: 10905–10913, ( 1995).

Toyota et al; "First total Synthesis of (±)–Methyl Gummiferolate Using a Homoallyl–Homoallyl Radical Rearrangement Reaction", 1(10): 1627–1629, (1999).

Paterson et al; "Studies in Marine Macrolide Synthesis: Stereocontrolled Synthesis of the $C_1$–$C_{11}$ and $C_{15}$–$C_{27}$ Subunits of Aplyronine A", Tetrahedron Letters 39: 6037–6040, ( 1998).

Wender et al.; "Synthetic Studies on Arene–Olefin Cycloadditions. 11. Total Synthesis of (–)–Retigeranic Acid", Tetrahedron Letters 31(18): 2517–2520, ( 1990).

Brion et al; "Stereoselective synthesis of a Trans–Octahydroindole Drivative. Precursor of Trandolapril (RU 44 570), an Inhibitor of Angiotensin Converting Enzyme", Tetrahedron Letters 33(34): 4889–4892, ( 1992).

Suzuki et al; "A Simple Synthesis of Bicyclo [2.2.1] Heptane System, A Key Potential Intermediate for Stable Prostaglandin $H_2$ Analogue", Heterocycles 14(11): 1735–1738, (1980).

Berkowitz et al.; "Enzyme Assisted Asymmetric total Synthesis of (– ) –Podophyllotoxin and (–)– Picropodophyllin", J. Org. Chem. 65: 847–860, (2000).

Ozegowski et al. "The Different Behaviour of Syn–and Anti–2,3 Dimethylbutanedioic Anhydride in the Lipase–Catalyzed Enantioselective Alcoholysis" Tetrahedron Asymmetry 6(5): 1191–1194, (1995).

Yamamoto et al.; Asymmetric Ring Opening of Cyclic Acid Anhydridess With Lipase in Organic Solvents, Tetrahedron Letters, pp. 1717–1720, (1988).

Yamamoto et al. "Asymmetric Synthesis of Optically Active Lactones from Cyclic Acid Anhydrides Using Lipase in Organic Solvents", Agric. Biol. Chem. 52(12): 3087–3092, (1988).

* cited by examiner

| Entry | Catalyst | Solvent | ee (%) of Product |
|---|---|---|---|
| 1 | Quinidine | Toluene | 64 |
| 2 | $(DHQD)_2PYR$ | Toluene | 13 |
| 3 | $(DHQD)_2PHAL$ | Toluene | 18 |
| 4 | $(DHQD)_2AQN$ | Toluene | 85 |
| 5 | DHQD-PHN | Toluene | 81 |
| 6 | DHQD-CLB | Toluene | 32 |
| 7 | DHQD-MEQ | Toluene | 31 |
| 8 | $(DHQD)_2AQN$ | $CCl_4$ | 88 |
| 9 | $(DHQD)_2AQN$ | $Et_2O$ | 93 |
| 10 | $(DHQD)_2AQN$ | $CHCl_3$ | 82 |
| 11 | $(DHQD)_2AQN$ | Hexane | 54 |
| 12 | $(DHQD)_2AQN$ | THF | 89 |
| 13 | $(DHQD)_2AQN$ | $^tBuOMe$ | 92 |
| 14 | $(DHQD)_2AQN$ | MeCN | 71 |
| 15 | $(DHQD)_2AQN$ | $CH_2Cl_2$ | 73 |

Figure 2

*meso* cyclic anhydride
(DHQD)$_2$AQN, MeOH
chiral non-racemic product 60-95% yield

| Entry | Anhydride | Catalyst Loading (mole %) | Solvent | Temp. (°C ) | ee (%)[c] | Product[b] |
|---|---|---|---|---|---|---|
| 1 | 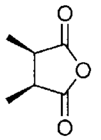 | 5 | Ether | -20 | 98 (98) | 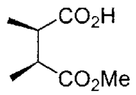 |
| 2 | 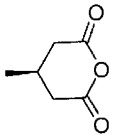 | 30 | Ether | -35 | 91 (82) | 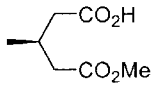 |
| 3 | 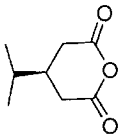 | 30 | Ether | -35 | 90 (83) | b 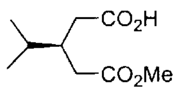 |
| 4 | 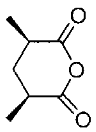 | 10 | Toluene | r.t. | 76[a] | 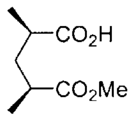 |

a: (DHQD)$_2$PHAL was used as catalyst. b: the absolute configuration was determined by comparison with authentic samples prepared by known procedure. c: the ee was determined by chiral GC or following a literature procedure. Enantiomeric excesses in parentheses were obtained using (DHQ)$_2$AQN as catalyst; the products obtained in these cases were of the opposite absolute configurations.

Figure 3

*meso* cyclic anhydride
(DHQD)$_2$AQN, MeOH
chiral non-racemic product 60-95% yield

| Entry | Anhydride | Catalyst Loading (mole %) | Solvent | Temp. ($^0$C ) | ee (%)[c] | Product[b] |
|---|---|---|---|---|---|---|
| 5 | 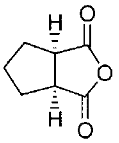 | 10 | Ether | -30 | 96 | 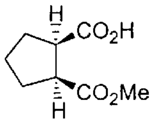 |
| 6 | 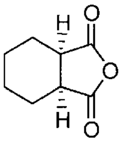 | 5 | Ether | -20 | 97 | 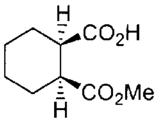 |
| 7 | 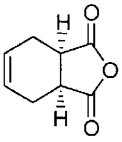 | 7 | Ether | -20 | 98 | b 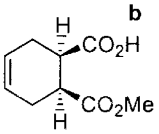 |
| 8 | 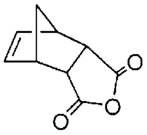 | 10 | Ether | -30 | 98 | b 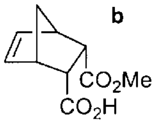 |

a: (DHQD)$_2$PHAL was used as catalyst. b: the absolute configuration was determined by comparison with authentic samples prepared by known procedure. c: the ee was determined by chiral GC or following a literature procedure.

Figure 4

*meso* cyclic anhydride — $(DHQD)_2AQN$, MeOH → chiral non-racemic product 60-95% yield

| Entry | Anhydride | Catalyst Loading (mole %) | Solvent | Temp. (°C ) | ee (%)[c] | Product[b] |
|---|---|---|---|---|---|---|
| 9 | 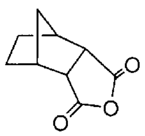 | 15 | Ether | -30 | 90 | 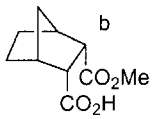 b |
| 10 | 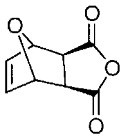 | 20 | Ether | -20 | 95 | 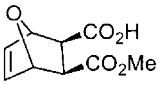 |
| 11 | 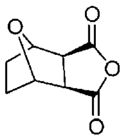 | 15 | Ether | -20 | 92 | 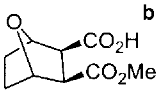 b |

a: $(DHQD)_2PHAL$ was used as catalyst. b: the absolute configuration was determined by comparison with authentic samples prepared by known procedure. c: the ee was determined by chiral GC or following a literature procedure.

Figure 5
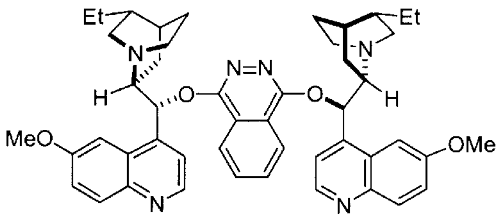
(DHQ)$_2$PHAL
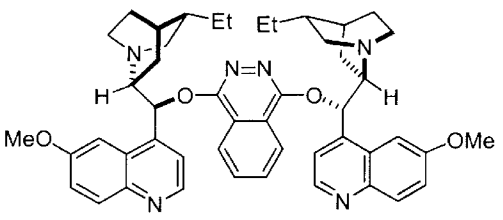
(DHQD)$_2$PHAL
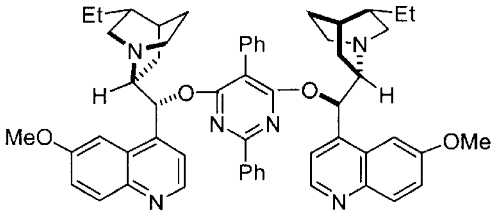
(DHQ)$_2$PYR
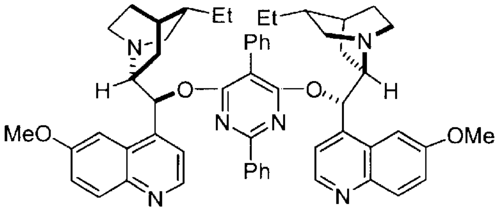
(DHQD)$_2$PYR
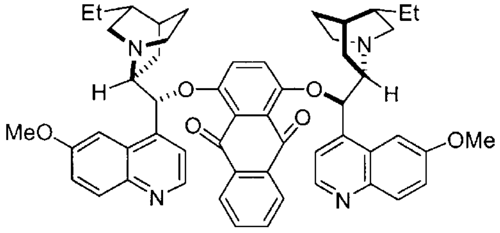
(DHQ)$_2$AQN
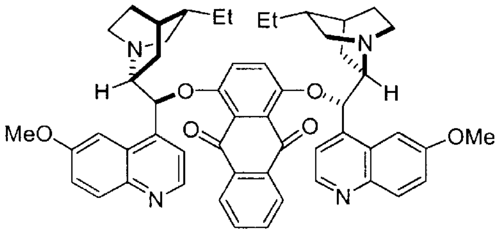
(DHQD)$_2$AQN Figure 6
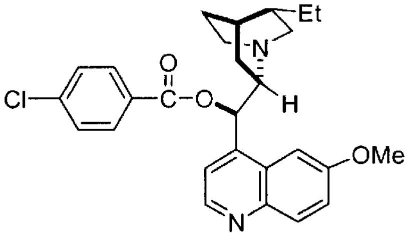
DHQ-CLB
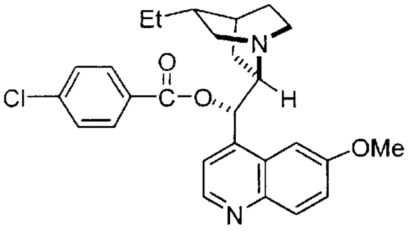
DHQD-CLB
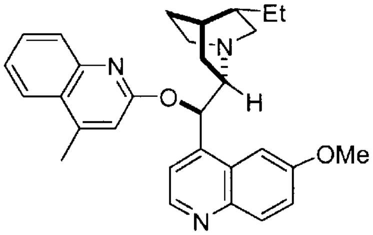
DHQ-MEQ
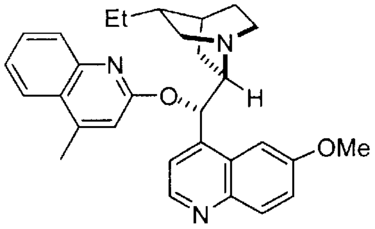
DHQD-MEQ
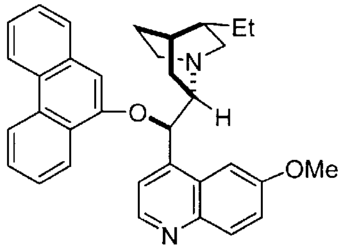
DHQ-AQN
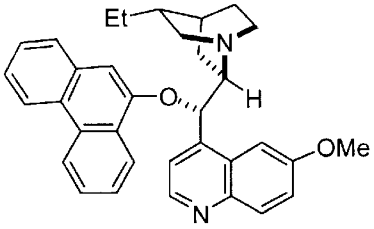
DHQD-AQN
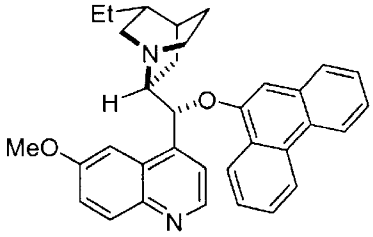
DHQ-PHN
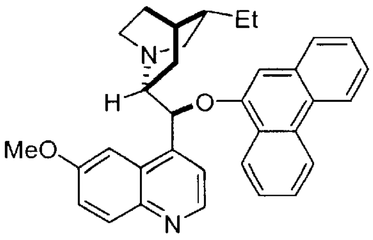
DHQD-PHN

Figure 7
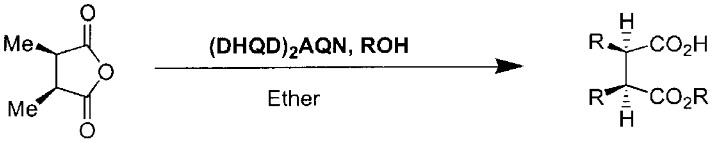
| Entry | ROH | Catalyst Loading (mole %) | Solvent | Temp. ($^0$C ) | ee (%) | Product |
|---|---|---|---|---|---|---|
| 1 | MeOH | 5 | Ether | r.t. | 93 | 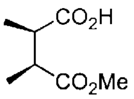 |
| 2 | EtOH | 5 | Ether | r.t. | 95 | 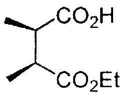 |
| 3 | EtOH | 10 | Ether | r.t. | 97 | 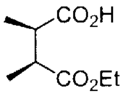 |
| 4 | iPrOH | 10 | Ether | r.t. | | No Reaction |

Figure 8

*meso* cyclic anhydride
DHQD-PHN, MeOH
chiral non-racemic product

| Entry | Anhydride | Catalyst Loading (mole %) | Solvent | Temp. ($^0$C) | ee (%)[a] | Product[b] |
|---|---|---|---|---|---|---|
| 1 | 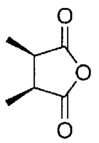 | 5<br>15<br>30 | Toluene<br>Toluene<br>Toluene | r.t.<br>-30<br>-30 | 81<br>95<br>96 | 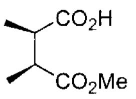 |
| 2 | 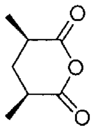 | 10 | Toluene | r.t. | 19 | 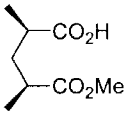 |
| 3 | 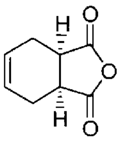 | 5 | Ether | r.t. | 88 | b 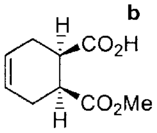 |
| 4 | 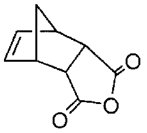 | 3 | $CCl_4$ | r.t. | 78 | b 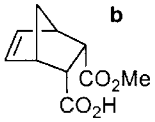 |

a: ee was determined by chiral GC or by following published procedure. b: the absolute configuration was determined by comparison with authentic samples prepared by a published procedure.

$^{13}C$ NMR ($CDCl_3$, 100 MHz)

CATALYTIC ASYMMETRIC DESYMMETRIZATION OF MESO COMPOUNDS

RELATED APPLICATIONS

This application claims the benefit of the filing date of U.S. Provisional Patent Application Ser. No. 60/194,520, filed Apr. 4, 2000.

BACKGROUND OF THE INVENTION

The demand for enantiomerically pure compounds has grown rapidly in recent years. One important use for such chiral, non-racemic compounds is as intermediates for synthesis in the pharmaceutical industry. For instance, it has become increasingly clear that enantiomerically pure drugs have many advantages over racemic drug mixtures. These advantages (reviewed in, e.g., Stinson, S. C., *Chem Eng News,* Sep. 28, 1992, pp. 46–79) include the fewer side effects and greater potency often associated with enantiomerically pure compounds.

Traditional methods of organic synthesis were often optimized for the production of racemic materials. The production of enantiomerically pure material has historically been achieved in one of two ways: use of enantiomerically pure starting materials derived from natural sources (the so-called "chiral pool"); and the resolution of racemic mixtures by classical techniques. Each of these methods has serious drawbacks, however. The chiral pool is limited to compounds found in nature, so only certain structures and configurations are readily available. Resolution of racemates, which requires the use of resolving agents, may be inconvenient and time-consuming. Furthermore, resolution often means that the undesired enantiomer is discarded, thus decreasing efficiency and wasting half of the material.

SUMMARY OF THE INVENTION

The present invention relates to methods for the synthesis of chiral non-racemic products, e.g., enantiomerically-enriched hemiesters, from prochiral starting materials, e.g., meso anhydrides. The present invention also relates to catalysts for the aforementioned methods, and methods for synthesizing these catalysts.

BRIEF DESCRIPTION OF THE DRAWINGS

FIG. 2 presents the enantiomeric excesses of the products obtained from the asymmetric desymmetrization of various meso cyclic anhydrides, as a function of the reaction conditions used.

FIG. 3 presents the enantiomeric excesses of the products obtained from the asymmetric desymmetrization of various meso cyclic anhydrides, as a function of the reaction conditions used.

FIG. 4 presents the enantiomeric excesses of the products obtained from the asymmetric desymmetrization of various meso cyclic anhydrides, as a function of the reaction conditions used.

FIG. 5 depicts the structures of certain catalysts used in the methods of the present invention, and the abbreviations used herein for them.

FIG. 6 depicts the structures of certain catalysts used in the methods of the present invention, and the abbreviations used herein for them.

FIG. 7 depicts the enantiomeric excesses of the products obtained from the a symmetric desymmetrization of various meso cyclic anhydrides, as a function of the reaction conditions used.

FIG. 8 depicts the enantiomeric excesses of the products obtained from the asymmetric desymmetrization of various meso cyclic anhydrides, as a function of the reaction conditions used.

DETAILED DESCRIPTION OF THE INVENTION

Figure 1:
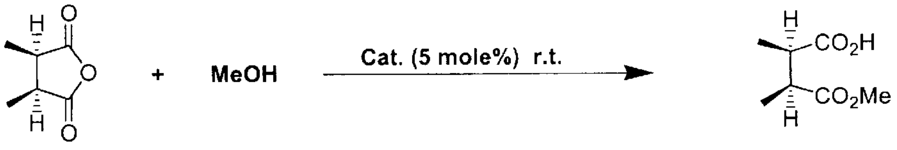
FIG. 1 presents the enantiomeric excess of the product obtained from the asymmetric desymmetrization of cis-2,3-dimethylsuccinic anhydride, as a function of the solvent and the catalyst used.
Figure 9:
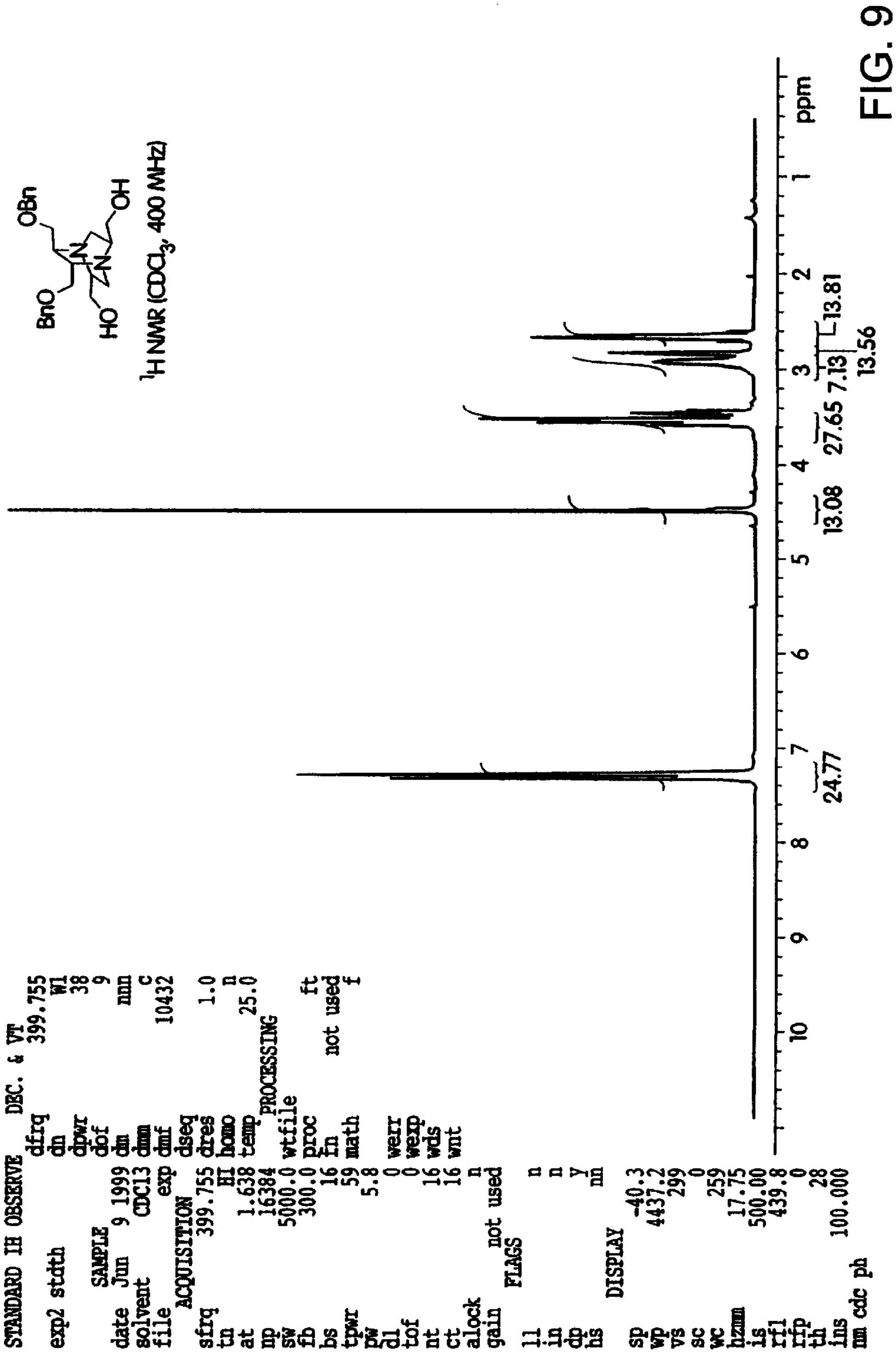
FIG. 9 depicts the $^{1}H$ NMR spectrum of a tertiary amine catalyst of the present invention, synthesized using the method of the present invention described in Example 2.
Figure 10:
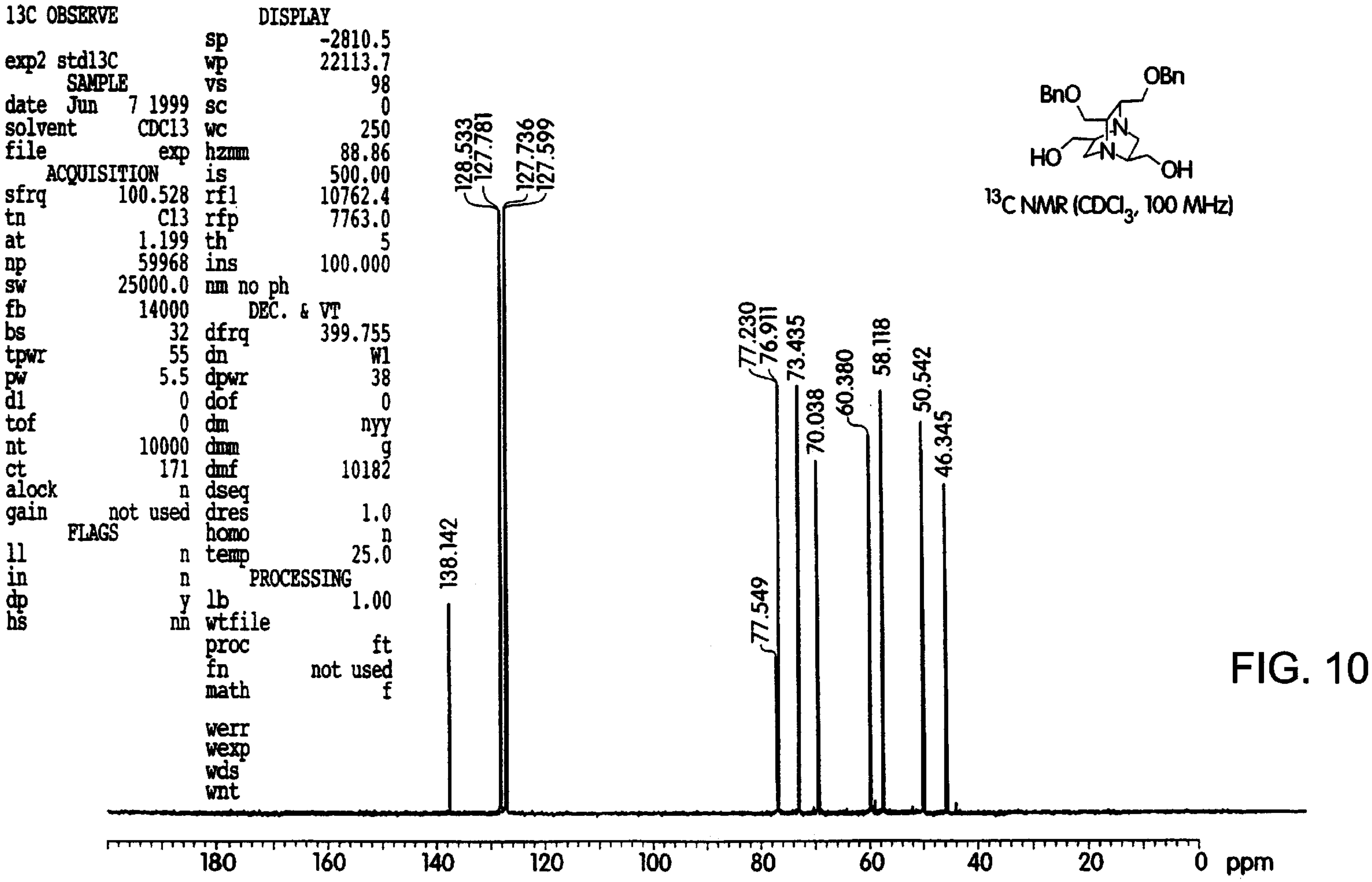
FIG. 10 depicts the $^{13}C$ NMR spectrum of a tertiary amine catalyst of the present invention, synthesized using the method of the present invention described in Example 2.

The ability to selectively transform a prochiral meso compound to a enantiomerically enriched or enantiomerically pure chiral compound has broad application, especially in the agricultural and pharmaceutical industries, as well as in the polymer industry. As described herein, the present invention relates to methods and catalysts for the catalytic asymmetric desymmetrization of prochiral meso compounds and the like. The primary constituents of the methods, which are set forth in detail below, are: a non-racemic chiral tertiary-amine-containing catalyst; a prochiral meso substrate, typically a heterocycle comprising a pair of electrophilic atoms related by an internal plane or point of symmetry; and a nucleophile, typically the solvent, which under the reaction conditions selectively attacks one of the two aforementioned electrophilic atoms, generating an enantiomerically enriched chiral product. Additionally, the catalysts and methods of the present invention can be exploited to effect kinetic resolutions of racemic mixtures and the like.

Definitions

For convenience, certain terms employed in the specification, examples, and appended claims are collected here.

The term "nucleophile" is recognized in the art, and as used herein means a chemical moiety having a reactive pair of electrons. Examples of nucleophiles include uncharged compounds such as water, amines, mercaptans and alcohols, and charged moieties such as alkoxides, thiolates, carbanions, and a variety of organic and inorganic anions. Illustrative anionic nucleophiles include simple anions such as hydroxide, azide, cyanide, thiocyanate, acetate, formate or chloroformate, and bisulfite. Organometallic reagents such as organocuprates, organozincs, organolithiums, Grignard reagents, enolates, acetylides, and the like may, under appropriate reaction conditions, be suitable nucleophiles. Hydride may also be a suitable nucleophile when reduction of the substrate is desired.

The term "electrophile" is art-recognized and refers to chemical moieties which can accept a pair of electrons from a nucleophile as defined above. Electrophiles useful in the method of the present invention include cyclic compounds such as epoxides, aziridines, episulfides, cyclic sulfates, carbonates, lactones, lactams and the like. Non-cyclic electrophiles include sulfates, sulfonates (e.g. tosylates), chlorides, bromides, iodides, and the like The terms "electrophilic atom", "electrophilic center" and "reactive center" as used herein refer to the atom of the substrate which is attacked by, and forms a new bond to, the nucleophile. In most (but not all) cases, this will also be the atom from which the leaving group departs.

The term "electron-withdrawing group" is recognized in the art and as used herein means a functionality which draws electrons to itself more than a hydrogen atom would at the same position. Exemplary electron-withdrawing groups include nitro, ketone, aldehyde, sulfonyl, trifluoromethyl, —CN, chloride, and the like. The term "electron-donating group", as used herein, means a functionality which draws electrons to itself less than a hydrogen atom would at the same position. Exemplary electron-donating groups include amino, methoxy, and the like.

The terms "Lewis base" and "Lewis basic" are recognized in the art, and refer to a chemical moiety capable of donating a pair of electrons under certain reaction conditions. Examples of Lewis basic moieties include uncharged compounds such as alcohols, thiols, olefins, and amines, and charged moieties such as alkoxides, thiolates, carbanions, and a variety of other organic anions.

The terms "Lewis acid" and "Lewis acidic" are art-recognized and refer to chemical moieties which can accept a pair of electrons from a Lewis base.

The term "meso compound" is recognized in the art and means a chemical compound which has at least two chiral centers but is achiral due to an internal plane, or point, of symmetry.

The term "chiral" refers to molecules which have the property of non-superimposability on their mirror image partner, while the term "achiral" refers to molecules which are superimposable on their mirror image partner. A "prochiral molecule" is an achiral molecule which has the potential to be converted to a chiral molecule in a particular process.

The term "stereoisomers" refers to compounds which have identical chemical constitution, but differ with regard to the arrangement of their atoms or groups in space. In particular, the term "enantiomers" refers to two stereoisomers of a compound which are non-superimposable mirror images of one another. The term "diastereomers", on the other hand, refers to the relationship between a pair of stereoisomers that comprise two or more asymmetric centers and are not mirror images of one another.

Furthermore, a "stereoselective process" is one which produces a particular stereoisomer of a reaction product in preference to other possible stereoisomers of that product. An "enantioselective process" is one which favors production of one of the two possible enantiomers of a reaction product. The subject method is said to produce a "stereoselectively-enriched" product (e.g., enantioselectively-enriched or diastereoselectively-enriched) when the yield of a particular stereoisomer of the product is greater by a statistically significant amount relative to the yield of that stereoisomer resulting from the same reaction run in the absence of a chiral catalyst. For example, an enantioselective reaction catalyzed by one of the subject chiral catalysts will yield an e.e. for a particular enantiomer that is larger than the e.e. of the reaction lacking the chiral catalyst.

The term "regioisomers" refers to compounds which have the same molecular formula but differ in the connectivity of the atoms. Accordingly, a "regioselective process" is one which favors the production of a particular regioisomer over others, e.g., the reaction produces a statistically significant preponderence of a certain regioisomer.

The term "reaction product" means a compound which results from the reaction of a nucleophile and a substrate. In general, the term "reaction product" will be used herein to refer to a stable, isolable compound, and not to unstable intermediates or transition states.

The term "substrate" is intended to mean a chemical compound which can react with a nucleophile, or with a ring-expansion reagent, according to the present invention, to yield at least one product having a stereogenic center.

The term "catalytic amount" is recognized in the art and means a substoichiometric amount relative to a reactant. As used herein, a catalytic amount means from 0.0001 to 90 mole percent relative to a reactant, more preferably from 0.001 to 50 mole percent, still more preferably from 0.01 to 10 mole percent, and even more preferably from 0.1 to 5 mole percent relative to a reactant.

As discussed more fully below, the reactions contemplated in the present invention include reactions which are enantioselective, diastereoselective, and/or regioselective. An enantioselective reaction is a reaction which converts an achiral reactant to a chiral product enriched in one enantiomer. Enantioselectivity is generally quantified as "enantiomeric excess" (ee) defined as follows:

$$\%\text{ Enantiomeric Excess } A\ (ee)=(\%\text{ Enantiomer } A)-(\%\text{ Enantiomer } B)$$

where A and B are the enantiomers formed. Additional terms that are used in conjunction with enatioselectivity include "optical purity" or "optical activity". An enantioselective reaction yields a product with an e.e. greater than zero. Preferred enantioselective reactions yield a product with an e.e. greater than 20%, more preferably greater than 50%, even more preferably greater than 70%, and most preferably greater than 80%.

A diastereoselective reaction converts a chiral reactant (which may be racemic or enantiomerically pure) to a product enriched in one diastereomer. If the chiral reactant is racemic, in the presence of a chiral non-racemic reagent or catalyst, one reactant enantiomer may react more slowly than the other. This class of reaction is termed a kinetic resolution, wherein the reactant enantiomers are resolved by differential reaction rate to yield both enantiomerically-enriched product and enantimerically-enriched unreacted substrate. Kinetic resolution is usually achieved by the use of sufficient reagent to react with only one reactant enantiomer (i.e. one-half mole of reagent per mole of racemic substrate). Examples of catalytic reactions which have been used for kinetic resolution of racemic reactants include the Sharpless epoxidation and the Noyori hydrogenation.

A regioselective reaction is a reaction which occurs preferentially at one reactive center rather than another non-identical reactive center. For example, a regioselective reaction of an unsymmetrically substituted epoxide substrate would involve preferential reaction at one of the two epoxide ring carbons.

The term "non-racemic" with respect to the chiral catalyst, means a preparation of catalyst having greater than 50% of a given enantiomer, more preferably at least 75%. "Substantially non-racemic" refers to preparations of the catalyst which have greater than 90% ee for a given enantiomer of the catalyst, more preferably greater than 95% ee.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In preferred embodiments, a straight chain or branched chain alkyl has 30 or fewer carbon atoms in its backbone (e.g., $C_1$–$C_{30}$ for straight chain, $C_3$–$C_{30}$ for branched chain), and more preferably 20 of fewer. Likewise, preferred cycloalkyls have from 4–10 carbon atoms in their ring structure, and more preferably have 5, 6 or 7 carbons in the ring structure.

Moreover, the term alkyl as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, a halogen, a hydroxyl, a carbonyl, an alkoxyl, and ester, a phosphoryl, an amine, an amide, an imine, a thiol, a thioether, a thioester, a sulfonyl, an amino, a nitro, or an organometallic moiety. It will be understood by those skilled in the art that the moieties substituted on the hydrocarbon chain can themselves be substituted, if appropriate. For instance, the substituents of a substituted alkyl may include substituted and unsubstituted forms of arnines, imines, amides, phosphoryls (including phosphonates and phosphines), sulfonyls (including sulfates and sulfonates), and silyl groups, as well as ethers, thioethers, selenoethers, carbonyls (including ketones, aldehydes, carboxylates, and esters), —$CF_3$, —CN and the like. Exemplary substituted alkyls are described below. Cycloalkyls can be further substituted with alkyls, alkenyls, alkoxys, thioalkyls, aminoalkyls, carbonyl-substituted alkyls, $CF_3$, CN, and the like.

The terms "alkenyl" and "alkynyl" refer to unsaturated aliphatic groups analogous in length and possible substitution to the alkyls described above, but which contain at least one double or triple carbon—carbon bond, respectively.

Unless the number of carbons is otherwise specified, "lower alkyl" as used herein means an alkyl group, as defined above, but having from one to ten carbons, more preferably from one to six carbon atoms in its backbone structure. Likewise, "lower alkenyl" and "lower alkynyl" have similar chain lengths.

As used herein, the term "amino" means —$NH_2$; the term "nitro" means —$NO_2$; the term "halogen" designates —F, —Cl, —Br or —I; the termn "thiol" means —SH; the term "hydroxyl" means —OH; the term "sulfonyl" means —$SO_2$—; and the term "organometallic" refers to a metallic atom (such as mercury, zinc, lead, magnesium or lithium) or a metalloid (such as silicon, arsenic or selenium) which is bonded directly to a carbon atom, such as a diphenylmethylsilyl group.

The terms "amine" and "amino" are art-recognized and refer to both unsubstituted and substituted amines, e.g., a moiety that can be represented by the general formula:

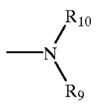 or 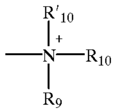

wherein $R_9$, $R_{10}$ and $R'_{10}$ each independently represent a group permitted by the rules of valence.

The term "acylamino" is art-recognized and refers to a moiety that can be represented by the general formula:

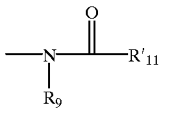

wherein $R_9$ is as defined above, and $R'_{11}$ represents a hydrogen, an alkyl, an alkenyl or —$(CH_2)_m$—$R_8$, where m and $R_8$ are as defined above.

The term "amido" is art recognized as an amino-substituted carbonyl and includes a moiety that can be represented by the general formula:

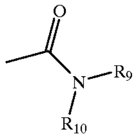

wherein $R_9$, $R_{10}$ are as defined above. Preferred embodiments of the amide will not include imides which may be unstable.

The term "alkylthio" refers to an alkyl group, as defined above, having a sulfur radical attached thereto. In preferred embodiments, the "alkylthio" moiety is represented by one of —S-alkyl, —S-alkenyl, —S-alkynyl, and —S—$(CH_2)_m$—$R_8$, wherein m and $R_8$ are defined above. Representative alkylthio groups include methylthio, ethyl thio, and the like.

The term "carbonyl" is art recognized and includes such moieties as can be represented by the general formula:

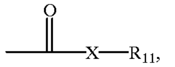 or 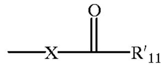

wherein X is a bond or represents an oxygen or a sulfur, and $R_{11}$ represents a hydrogen, an alkyl, an alkenyl, —$(CH_2)_m$—$R_8$ or a pharmaceutically acceptable salt, $R'_{11}$ represents a hydrogen, an alkyl, an alkenyl or —$(CH_2)_m$—$R_8$, where m and $R_8$ are as defined above. Where X is an oxygen and $R_{11}$ or $R'_{11}$ is not hydrogen, the formula represents an "ester". Where X is an oxygen, and $R_{11}$ is as defined above, the moiety is referred to herein as a carboxyl group, and particularly when $R_{11}$ is a hydrogen, the formula represents a "carboxylic acid". Where X is an oxygen, and $R'_{11}$ is hydrogen, the formula represents a "formate". In general, where the oxygen atom of the above formula is replaced by sulfur, the formula represents a "thiolcarbonyl" group. Where X is a sulfur and $R_{11}$ or $R'_{11}$ is not hydrogen, the formula represents a "thiolester." Where X is a sulfur and $R_{11}$ is hydrogen, the formula represents a "thiolcarboxylic acid." Where X is a sulfur and $R_{11'}$ is hydrogen, the formula represents a "thiolformate." On the other hand, where X is a bond, and $R_{11}$ is not hydrogen, the above formula represents a "ketone" group. Where X is a bond, and $R_{11}$ is hydrogen, the above formula represents an "aldehyde" group.

The terms "alkoxyl" or "alkoxy" as used herein refers to an alkyl group, as defined above, having an oxygen radical attached thereto. Representative alkoxyl groups include methoxy, ethoxy, propyloxy, tert-butoxy and the like. An "ether" is two hydrocarbons covalently linked by an oxygen. Accordingly, the substituent of an alkyl that renders that alkyl an ether is or resembles an alkoxyl, such as can be represented by one of —O-alkyl, —O-alkenyl, —O-alkynyl, —O—$(CH_2)_m$—$R_8$, where m and $R_8$ are described above.

The term "sulfonate" is art recognized and includes a moiety that can be represented by the general formula:

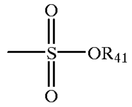

in which $R_{41}$ is an electron pair, hydrogen, alkyl, cycloalkyl, or aryl.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, Ms represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The term "sulfonylamino" is art recognized and includes a moiety that can be represented by the general formula:

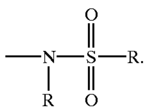

The term "sulfamoyl" is art-recognized and includes a moiety that can be represented by the general formula:

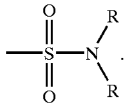

The term "sulfonyl", as used herein, refers to a moiety that can be represented by the general formula:

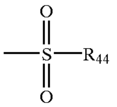

in which $R_{44}$ is selected from the group consisting of hydrogen, alkyl, alkenyl, alkynyl, cycloalkyl, heterocyclyl, aryl, or heteroaryl.

The term "sulfoxido" as used herein, refers to a moiety that can be represented by the general formula:

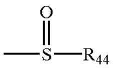

in which $R_{44}$ is selected from the group consisting of hydrogen, alkyl, alkenyl, alkynyl, cycloalkyl, heterocyclyl, aralkyl, or aryl.

The term "sulfate", as used herein, means a sulfonyl group, as defined above, attached to two hydroxy or alkoxy groups. Thus, in a preferred embodiment, a sulfate has the structure:

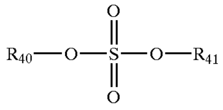

in which $R_{40}$ and $R_{41}$ are independently absent, a hydrogen, an alkyl, or an aryl. Furthermore, $R_{40}$ and $R_{41}$, taken together with the sulfonyl group and the oxygen atoms to which they are attached, may form a ring structure having from 5 to 10 members.

Analogous substitutions can be made to alkenyl and alkynyl groups to produce, for example, alkenylamines, alkynylamines, alkenylamides, alkynylamides, alkenylimines, alkynylimines, thioalkenyls, thioalkynyls, carbonyl-substituted alkenyls or alkynyls, alkenoxyls, alkynoxyls, metalloalkenyls and metalloalkynyls.

The term "aryl" as used herein includes 4-, 5-, 6- and 7-membered single-ring aromatic groups which may include from zero to four heteroatoms, for example, benzene, pyrrole, furan, thiophene, imidazole, oxazole, thiazole, triazole, pyrazole, pyridine, pyrazine, pyridazine and pyrimidine, and the like. Those aryl groups having heteroatoms in the ring structure may also be referred to as "aryl heterocycle". The aromatic ring can be substituted at one or more ring positions with such substituents as described above, as for example, halogens, alkyls, alkenyls, alkynyls, hydroxyl, amino, nitro, thiol amines, imines, amides, phosphonates, phosphines, carbonyls, carboxyls, silyls, ethers, thioethers, sulfonyls, selenoethers, ketones, aldehydes, esters, or $-(CH_2)_m-R_7$, $-CF_3$, $-CN$, or the like.

The terms "heterocycle" or "heterocyclic group" refer to 4 to 10-membered ring structures, more preferably 5 to 7 membered rings, which ring structures include one to four heteroatoms. Heterocyclic groups include pyrrolidine, oxolane, thiolane, imidazole, oxazole, piperidine, piperazine, morpholine. The heterocyclic ring can be substituted at one or more positions with such substituents as described above, as for example, halogens, alkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, or $-(CH_2)_m-R_7$, $-CF_3$, $-CN$, or the like.

The terms "polycycle" or "polycyclic group" refer to two or more cyclic rings (e.g., cycloalkyls, cycloalkenyls, cycloalkynyls, aryls and/or heterocycles) in which two or more carbons are common to two adjoining rings, e.g., the rings are "fused rings". Rings that are joined through non-adjacent atoms are termed "bridged" rings. Each of the rings of the polycycle can be substituted with such substituents as described above, as for example, halogens, alkyls, alkenys, alkynyls, hydroxyl, amino, nitro, thiol, amines, imines, amides, phosphonates, phospbines, carbonyls, carboxyls, silyls, ethers, thioethers, sulfonyls, selenoethers, ketones, aldehydes, esters, or $-(CH_2)_m-R_7$, $-CF_3$, $-CN$, or the like.

The term "heteroatom" as used herein means an atom of any element other than carbon or hydrogen. Preferred heteroatoms are nitrogen, oxygen, sulfur, phosphorus and selenium.

For purposes of this invention, the chemical elements are identified in accordance with the Periodic Table of the Elements, CAS version, Handbook of Chemistry and Physics, 67th Ed., 1986–87, inside cover. Also for purposes of this invention, the term "hydrocarbon" is contemplated to include all permissible compounds having at least one hydrogen and one carbon atom. In a broad aspect, the permissible hydrocarbons include acyclic and cyclic, branched and unbranched, carbocyclic and heterocyclic, aromatic and nonaromatic organic compounds which can be substituted or unsubstituted.

The terms ortho, meta and para apply to 1,2-, 1,3- and 1,4-disubstituted benzenes, respectively. For example, the names 1,2-dimethylbenzene and ortho-dimethylbenzene are synonymous.

The terms triflyl, tosyl, mesyl, and nonaflyl are art-recognized and refer to trifluoromethanesulfonyl, p-toluenesulfonyl, methanesulfonyl, and nonafluorobutanesulfonyl groups, respectively. The terms triflate, tosylate, mesylate, and nonaflate are art-recognized and refer to trifluoromethanesulfonate ester, p-toluenesulfonate ester, methanesulfonate ester, and nonafluorobutanesulfonate ester functional groups and molecules that contain said groups, respectively.

The abbreviations Me, Et, Ph, Tf, Nf, Ts, and Ms, represent methyl, ethyl, phenyl, trifluoromethanesulfonyl, nonafluorobutanesulfonyl, p-toluenesulfonyl and methanesulfonyl, respectively. A more comprehensive list of the abbreviations utilized by organic chemists of ordinary skill in the art appears in the first issue of each volume of the *Journal of Organic Chemistry;* this list is typically presented in a table entitled *Standard List of Abbreviations.* The abbreviations contained in said list, and all abbreviations utilized by organic chemists of ordinary skill in the art are hereby incorporated by reference.

The phrase "protecting group" as used herein means temporary substituents which protect a potentially reactive functional group from undesired chemical transformations. Examples of such protecting groups include esters of carboxylic acids, silyl ethers of alcohols, and acetals and ketals of aldehydes and ketones, respectively. The field of protecting group chemistry has been reviewed (Greene, T. W.; Wuts, P. G. M. *Protective Groups in Organic Synthesis, 2nd* ed.; Wiley: New York, 1991).

As used herein, the term "substituted" is contemplated to include all permissible substituents of organic compounds. In a broad aspect, the permissible substituents include acyclic and cyclic, branched and unbranched, carbocyclic and heterocyclic, aromatic and nonaromatic substituents of organic compounds. Illustrative substituents include, for example, those described hereinabove. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Catalysts of the Invention

The catalysts employed in the subject methods are non-racemic chiral amines which present an asymmetric environment, causing differentiation between two or more moieties related by symmetry in a meso molecule, i.e., a molecule comprising at least two chiral centers, and an internal plane or point of symmetry or both. In general, catalysts intended by the present invention can be characterized in terms of a number of features. For instance, a salient aspect of each of the catalysts contemplated by the instant invention concerns the use of asymmetric bicyclic or polycyclic scaffolds incorporating the tertiary amine moiety which provide a rigid or semi-rigid environment near the amine nitrogen. This feature, through imposition of structural rigidity on the amine nitrogen in proximity to one or more asymmetric centers present in the scaffold, contributes to the creation of a meaningful difference in the energies of the corresponding diastereomeric transitions states for the overall transformation. Furthermore, the choice of substituents may also effect catalyst reactivity. For example, bulkier substituents on the catalyst are generally found to provide higher catalyst turnover numbers.

A preferred embodiment for each of the embodiments described above provides a catalyst having a molecular weight less than 2,000 g/mol, more preferably less than 1,000 g/mol, and even more preferably less than 500 g/mol. Additionally, the substituents on the catalyst can be selected to influence the solubility of the catalyst in a particular solvent system.

In certain embodiments, the chiral, non-racemic tertiary amine catalyst comprises a 1-azabicyclo[2.2.2]octane moiety or a 1,4-diazabicyclo[2.2.2]octane moiety. In certain embodiments, the chiral, non-racemic tertiary amine catalyst is a cinchona alkaloid, $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, or DHQD-PHN. In certain embodiments, the chiral, non-racemic tertiary amine catalyst is DHQD-PHN or $(DHQD)_2AQN$.

As mentioned briefly above, the choice of catalyst substituents can also effect the electronic properties of the catalyst. Substitution of the catalyst with electron-rich (electron-donating) moieties (including, for example, alkoxy or amino groups) may increase the electron density of the catalyst at the tertiary amine nitrogen, rendering it a stronger nucleophile and/or Bronsted base and/or Lewis base. Conversely, substitution of the catalyst with electron-poor moieties (for example, chloro or trifluoromethyl groups) can result in lower electron density of the catalyst at the tertiary amine nitrogen, rendering it a weaker nucleophile and/or Bronsted base and/or Lewis base. To summarize this consideration, the electron density of the catalyst can be important because the electron density at the tertairy amine nitrogen will influence the Lewis basicity of the nitrogen and its nucleophilicity. Choice of appropriate substituents thus makes possible the "tuning" of the reaction rate and the stereoselectivity of the reaction.

Methods of the Invention

Preparation of Asymmetric Tertiary Amine-Containg Catalysts

Certain aspects of the present invention relate to methods for preparing tertiary amines, which tertiary amine will be useful in the desymmetrization methods of the present invention. In certain embodiments, the tertiary amines are synthesized according to a general procedure, wherein a diamine is reacted with two equivalents of a chiral, non-racemic glycidyl sulfonate or halide. For example, the scheme below depicts an embodiment of these methods, wherein ethylene diamine and two equivalents of a chiral, non-racemic glycidyl nosylate react to give a chiral, non-racemic bis-tertiary amine. See also Example 2.

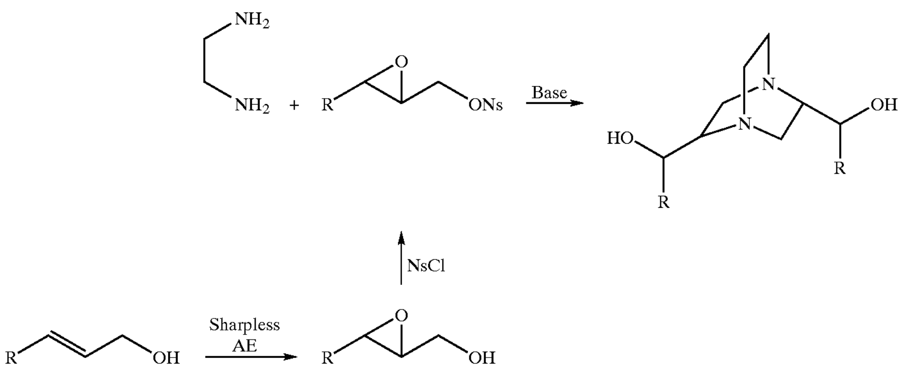

Methods of the Invention

Catalyzed Reactions

In one aspect of the present invention there is provided a process for stereoselectively producing compounds with at least one stereogenic center from meso starting materials. An advantage of this invention is that enantiomerically enriched products can be synthesized from prochiral or racemic reactants. Another advantage is that yield losses associated with the production of an undesired enantiomer can be substantially reduced or eliminated altogether.

In general, the invention features a stereoselective ring opening process which comprises combining a nucleophilic reactant, a prochiral or chiral cyclic substrate, and at least a catalytic amount of non-racemic chiral catalyst of particular characteristics (as described below). The cyclic substrate of the reaction will include a carbocycle or heterocycle which has an electrophilic atom susceptible to attack by the nucleophile. The combination is maintained under conditions appropriate for the chiral catalyst to catalyze stereoselective opening of the cyclic substrate at the electrophilic atom by reaction with the nucleophilic reactant. This reaction can be applied to enantioselective processes as well as diastereoselective processes. It may also be adapted for regioselective reactions. Examples of enantioselective reactions, kinetic resolutions, and regioselective reactions which may be catalyzed according to the present invention follow.

In another aspect of the present invention, kinetic resolution of enantiomers occurs by catalysis, using a subject chiral catalyst, of the tranformation of a racemic substrate. In the subject kinetic resolution processes for a racemic substrate, one enantiomer can be recovered as unreacted substrate while the other is transformed to the desired product. Of course, it will be appreciated that the kinetic resolution can be performed by removing the undesired enantiomer by reaction with a nucleophile, and recovering the desired enantiomer unchanged from the reaction mixture. One significant advantage of this approach is the ability to use inexpensive racemic starting materials rather than the expensive, enantiomerically pure starting compounds. In certain embodiments, the subject catalysts may be used in kinetic resolutions of racemic cyclic substrates wherein the nucleophile is a co-solvent. Suitable nucleophiles of this type include water, alcohols, and thiols.

The processes of this invention can provide optically active products with very high stereoselectivity (e.g., enantioselectivity or diastereoselectivity) or regioselectivity. In preferred embodiments of the subject desymmetrization reactions, products with enantiomeric excesses of greater than about 50%, greater than about 70%, greater than about 90%, and most preferably greater than about 95% can be obtained. The processes of this invention can also be carried out under reaction conditions suitable for commercial use, and typically proceed at reaction rates suitable for large scale operations.

In certain embodiments, the chiral, non-racemic tertiary amine catalyst is present in less than about 30 mol % relative to the prochiral starting material. In certain embodiments, the chiral, non-racemic tertiary amine catalyst is present in less than about 20 mol % relative to the prochiral starting material. In certain embodiments, the chiral, non-racemic tertiary amine catalyst is present in less than about 10 mol % relative to the prochiral starting material. In certain embodiments, the chiral, non-racemic tertiary amine catalyst is present in less than about 5 mol % relative to the prochiral starting material.

As is clear from the above discussion, the chiral products produced by the asymmetric synthesis processes of this invention can undergo further reaction(s) to afford desired derivatives thereof. Such permissible derivatization reactions can be carried out in accordance with conventional procedures known in the art. For example, potential derivatization reactions include esterification, N-alkylation of amides, and the like. The invention expressly contemplates the preparation of end-products and synthetic intermediates which are useful for the preparation or development or both of cardiovascular drugs, non-steroidal anti-inflammatory drugs, central nervous system agents, and antihistaminics.

Nucleophiles

Nucleophiles which are useful in the present invention may be determined by the skilled artisan according to several criteria. In general, a suitable nucleophile will have one or more of the following properties: 1) It will be capable of reaction with the substrate at the desired electrophilic site; 2) It will yield a useful product upon reaction with the substrate; 3) It will not react with the substrate at functionalities other than the desired electrophilic site; 4) It will react with the substrate at least partly through a mechanism catalyzed by the chiral catalyst; 5) It will not substantially undergo further undesired reaction after reacting with the substrate in the desired sense; and 6) It will not substantially react with or degrade the catalyst. It will be understood that while undesirable side reactions (such as catalyst degradation) may occur, the rates of such reactions can be rendered slow—through the selection of reactants and conditions—in comparison with the rate of the desired reaction(s).

Nucleophiles which satisfy the above criteria can be chosen for each substrate and will vary according to the substrate structure and the desired product. Routine experimentation may be necessary to determine the preferred nucleophile for a given transformation. For example, if a nitrogen-containing nucleophile is desired, it may be selected from ammonia, phthalimide, hydrazine, an amine or the like. Similarly, oxygen nucleophiles such as water, hydroxide, alcohols, alkoxides, siloxanes, carboxylates, or peroxides may be used to introduce oxygen; and mercaptans, thiolates, bisulfite, thiocyanate and the like may be used to introduce a sulfur-containing moiety. Additional nucleophiles will be apparent to those of ordinary skill in the art.

For nucleophiles which exist as anions, the counterion can be any of a variety of conventional cations, including alkali and alkaline earth metal cations and ammonium cations.

In certain embodiments, the nucleophile may be part of the substrate, thus resulting in an intramolecular reaction.

Substrates

As discussed above, a wide variety of substrates are useful in the methods of the present invention. The choice of substrate will depend on factors such as the nucleophile to be employed and the desired product, and an appropriate substrate will be apparent to the skilled artisan. It will be understood that the substrate preferably will not contain any interfering functionalities. In general, an appropriate substrate will contain at least a pair of reactive electrophilic centers or moieties related by an internal plane or point of symmetry at which a nucleophile may attack with the assistance of the catalyst. The catalyzed, stereoselective attack of the nucleophile at one of these electrophilic centers will produce a chiral non-racemic product.

Most of the substrates contemplated for use in the methods of the present invention contain at least one ring having three to seven atoms. Small rings are frequently strained, enhancing their reactivity. However, in some embodiments a cyclic substrate may not be strained, and may have a larger electrophilic ring.

Examples of suitable cyclic substrates which can be opened in the subject method include cyclic anhydrides, cyclic imides, and the like.

In preferred embodiments, the cyclic substrate is a meso compound. In other embodiments, the cyclic substrate will be a chiral compound. In certain embodiments, the substrate will be a racemic mixture. In certain embodiments, the substrate will be a mixture of diastereomers.

In certain embodiments, the electrophilic atom may be a heteroatom.

Reaction Conditions

The asymmetric reactions of the present invention may be performed under a wide range of conditions, though it will be understood that the solvents and temperature ranges recited herein are not limitative and only correspond to a preferred mode of the process of the invention.

In general, it will be desirable that reactions are run using mild conditions which will not adversely effect the substrate, the catalyst, or the product. For example, the reaction temperature influences the speed of the reaction, as well as the stability of the reactants, products, and catalyst. The reactions will usually be run at temperatures in the range of −78° C. to 100° C., more preferably in the range −20° C. to 50° C. and still more preferably in the range −20° C. to 25° C.

In general, the asymmetric synthesis reactions of the present invention are carried out in a liquid reaction medium. The reactions may be run without addition of solvent. Alternatively, the reactions may be run in an inert solvent, preferably one in which the reaction ingredients, including the catalyst, are substantially soluble. Suitable solvents include ethers such as diethyl ether, 1,2-dimethoxyethane, diglyme, t-butyl methyl ether, tetrahydrofuran and the like; halogenated solvents such as chloroform, dichloromethane, dichloroethane, chlorobenzene, and the like; aliphatic or aromatic hydrocarbon solvents such as benzene, toluene, hexane, pentane and the like; esters and ketones such as ethyl acetate, acetone, and 2-butanone; polar aprotic solvents such as acetonitrile, dimethylsulfoxide, dimethylformamide and the like; or combinations of two or more solvents. Furthermore, in certain embodiments it may be advantageous to employ a solvent which is not inert to the substrate under the conditions employed, e.g., use of ethanol as a solvent when ethanol is the desired nucleophile. In embodiments where water or hydroxide are not preferred nucleophiles, the reactions can be conducted under anhydrous conditions. In certain embodiments, ethereal solvents are preferred. In embodiments where water or hydroxide are preferred nucleophiles, the reactions are run in solvent mixtures comprising an appropriate amount of water and/or hydroxide.

The invention also contemplates reaction in a biphasic mixture of solvents, in an emulsion or suspension, or reaction in a lipid vesicle or bilayer. In certain embodiments, it may be preferred to perform the catalyzed reactions in the solid phase.

In some preferred embodiments, the reaction may be carried out under an atmosphere of a reactive gas. For example, desymmetrization with cyanide as nucleophile may be performed under an atmosphere of HCN gas. The partial pressure of the reactive gas may be from 0.1 to 1000 atmospheres, more preferably from 0.5 to 100 atm, and most preferably from about 1 to about 10 atm.

In certain embodiments it is preferable to perform the reactions under an inert atmosphere of a gas such as nitrogen or argon.

The asymmetric synthesis processes of the present invention can be conducted in continuous, semi-continuous or batch fashion and may involve a liquid recycle and/or gas recycle operation as desired. The processes of this invention are preferably conducted in batch fashion. Likewise, the manner or order of addition of the reaction ingredients, catalyst and solvent are also not critical and may be accomplished in any conventional fashion.

The reaction can be conducted in a single reaction zone or in a plurality of reaction zones, in series or in parallel or it may be conducted batchwise or continuously in an elongated tubular zone or series of such zones. The materials of construction employed should be inert to the starting materials during the reaction and the fabrication of the equipment should be able to withstand the reaction temperatures and pressures. Means to introduce and/or adjust the quantity of starting materials or ingredients introduced batchwise or continuously into the reaction zone during the course of the reaction can be conveniently utilized in the processes especially to maintain the desired molar ratio of the starting materials. The reaction steps may be effected by the incremental addition of one of the starting materials to the other. Also, the reaction steps can be combined by the joint addition of the starting materials to the optically active metal-ligand complex catalyst. When complete conversion is not desired or not obtainable, the starting materials can be separated from the product and then recycled back into the reaction zone.

The processes may be conducted in either glass lined, stainless steel or similar type reaction equipment. The reaction zone may be fitted with one or more internal and/or external heat exchanger(s) in order to control undue temperature fluctuations, or to prevent any possible "runaway" reaction temperatures.

Furthermore, the chiral catalyst can be immobilized or incorporated into a polymer or other insoluble matrix by, for example, covalently linking it to the polymer or solid support through one or more of its substituents. An immobilized catalyst may be easily recovered after the reaction, for instance, by filtration or centrifugation.

EXEMPLIFICATION

The invention now being generally described, it will be more readily understood by reference to the following examples which are included merely for purposes of illustration of certain aspects and embodiments of the present invention, and are not intended to limit the invention.

Example 1

Highly Enantioselective Catalytic Desymmetrization of Cyclic meso Anhydrides

Enantioselective opening of the readily accessible meso-cyclic anhydrides generates enantiomerically enriched chiral hemiesters containing one or multiple stereogenic centers and two chemically differentiated carbonyl functionalities (eq. 1). These optically active bifunctional hemiesters are versatile chiral building blocks in asymmetric synthesis.[1,2,3,4,5,6,7,8,9] Due to its great significance for organic synthesis, the development of highly enantio selective desymmetrization of meso-cyclic anhydrides has been a topic of intense research.[10,11,12,13,14,15] Synthetically useful selectivity has been obtained in desymmetrizations assisted by a stoichiometric amount of chiral auxiliaries or chiral mediators.[10,11] Despite considerable efforts,[11–15] the development of a general and effective catalytic desymmetrization of meso-cyclic anhydrides has not yet been achieved and therefore remains a desirable and highly challenging goal.

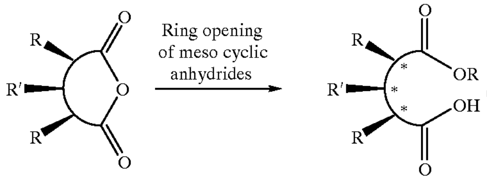

(eq. 1)

1a: R = H; R′ is not H
1b: R is not H; R′ = H
1c: R is not H; R′ is not H

2a: R = H; R′ is not H
2b: R is not H; R′ = H
2c: R is not H; R′ is not H

Our general interests in asymmetric catalysis of chiral Lewis bases lead our attention to amine-catalyzed alcoholysis of cyclic anhydride. Oda first reported that cinchona alkaloids catalyze asymmetric methanalysis of various mono and bicyclic anhydrides.[12] Atkin later extended this reaction to desymmetrize certain tricyclic anhydrides.[13] Although the reactions proceeded in good yield, the hemiesters were obtained in low to modest enantiomeric excess. We suspect that the unsatisfactory enantioselectivity may partially arise from the existence of a non-selective catalysis by the quinoline nitrogen since the monohydrochloride quinine is reported by Atkin to catalyze the methanolysis of the cyclic anhydride with no enantioselectivity.[13a] This quinoline nitrogen-catalyzed racemic pathway should become increasingly competitive as the reaction proceeds to high conversion when the rate of the quinuclidine nitrogen-catalyzed enantioselective reaction is expected to reduce significantly as a result of deactivation of the catalyst caused by protonation of the quinuclidine nitrogen by the acidic hemiester. In principle the racemic pathway could be suppressed by using analogs of cinchona alkaloids devoid of the quinoline nitrogen as the catalyst. The implementation of such an approach is, however, experimentally difficult due to the considerable synthetic effort required for the preparation of such analogs.[16] Furthermore, a large, if not stoichiometric, amount of the quinuclidine catalysts may be required to promote the reaction to go to completion. We are interested in exploring an alternative strategy of decreasing the basicity of the quinuclidine nitrogen, thereby shifting the equilibrium of the acid-base reaction towards the formation of the free amine catalyst. Such a strategy could lead to significant improvements in both the efficiency and the selectivity of the asymmetric catalysis through minimizing the deactivation of the free base amine catalyst by the acidic hemiester. Furthermore this approach could be easily implemented experimentally by changing the environment around the quinuclidine nitrogen via a simple modification of the cinchona alkaloid. We envisaged that a straightforward derivatizations of the C-9 alcohol with bulky alkyl or aryl groups could generate ethers of cinchona alkaloids with a decreased basicity of the quinuclidine nitrogen by destabilizing the ammonium ion x via the creation of a steric barrier for ion solvation. To this end, following the condition reported by Oda,[12] a variety of commercially available aryl ethers and esters of cinchona alkaloids are screened for their ability to catalyze enantioselective methanolysis of 2,3-dimethyl succinic anhydride (3). The results of our screening study are described in FIG. 1.

We were pleased to find that very good enantioselectivity is obtained with reactions mediated by aryl ethers of both a monocinchona (DHQD.PHN) and a biscinchona alkaloids $[(DHQD)_2AQN]$.[17] While both alkaloids are effective catalyst, the latter in general gives higher enantioselectivity. When one equivalent of anhydride 3 was treated with 10 equivalent of methanol in dry toluene in the presence of 5 mol % of either DHQD.PHN or $(DHQD)_2AQN$ as catalyst, the reaction went to completion in 2–4 hours to give the corresponding hemiester in 81% and 85% ee respectively. The structure of the aryl group of the modified cinchona alkaloids has a dramatic impact on the selectivity of the catalyst. While catalysts bearing bulky aromatic groups such as PHN and AQN afford high enantioselectivities, a dramatic deterioration in enantioselectivity was observed with catalysts bearing relatively small heterocyclic rings as substituents at O-9 position (entries 2, 3, 6, 7 in FIG. 1). The reaction can be further optimized to give the product in excellent ee (93% ee) at room temperature by using ether as the solvent.

Encouraged by these promising results, we investigated the catalytic desymmetrization of a wide variety of cyclic anhydrides. The results are summarized in FIGS. 2–4. The scope of the reaction is very general in giving excellent enantioselectivity and yield for the desymmetrization of a wide range of meso-cyclic anhydrides. Extraordinarily high enantioselectivity was observed for anhydride 3 as well as each of the bicyclic anhydrides employed in our investigation (entries 1, 5, 6 and 7 in FIGS. 2–4). Excellent enantioselectivities are obtained with monocyclic and tricyclic anhydrides (entries 2, 3, 8, 9, 10, and 11 in FIGS. 2–4) to give acyclic and bicyclic chiral hemiesters respectively in highly enantiomerically enriched form. Substrates containing heterocyclic rings other than the cyclic anhydride are also converted into the desired product in very high enantioselectivity (entries 10 and 11 in FIGS. 2–4). It is remarkable that even a monocyclic anhydride with a β-methyl substituent is transformed in 89% ee although a relatively high catalyst loading is required. The high enantioselectivity in the ring opening of 1,2-cyclopentylanhydride (entry 5 in FIGS. 2–4) is particularly noteworthy considering that it is significantly higher than that obtained by reactions using stoichiometric amount of chiral promoters.[11] Furthermore, synthetic routes based on hydrolytic enzymes can only provide the cyclopentyl hemiester in low ee. It is significant to note that when $(DHQ)_2AQN$ was employed to catalyze the ring opening of 2,3-dimethylsuccinic anhydride (3) the opposite enantiomer of the corresponding hemiester was obtained in 96% ee, thus proving that either enantiomers of the hemiesters can be prepared in a straightforward and highly enantioselective fashion via the reaction described here. We are surprised to find that $(DHQD)_2$ AQN-mediated ring opening of 2,4-dimethylglutaricanhydride gives the desired hemiester in good yield but in very low ee (30% ee). The enantioselectivity can, however, be improved significantly when the reaction is promoted by $(DHQD)_2PHAL$ (entry 4 in FIGS. 2–4).

We have performed a preparative scale reaction to demonstrate the practicality of this catalytic desymmetrization. Anhydride 3 was transformed on a 5 mmol scale to the corresponding hemiester in larger than 98% ee with a catalyst loading of 5 mol %. When the starting material was consumed (24 hour), a simple extraction of the reaction mixture with aqueous HCl (1 N) separates the catalyst from the product. Evaporation of the organic solvent provides the desired product in high purity (pure by NMR) and excellent yield (95%). The catalyst can be easily recovered quantitatively. Basifying the aqueous phase with KOH followed by extraction of the alkaline aqueous solution with EtOAc and removal of the organic solvent furnished the recovered catalyst in high purity (pure by NMR). The recovered catalyst is used without further treatment for another preparative scale reaction to give a new batch of product without deterioration in ee and yield.

We have demonstrated that the newly uncovered catalytic desymmetrization of meso-cyclic anhydrides mediated by the commercially available aryl ethers of chinchona alkaloids is a general, highly selective and practical catalytic asymmetric transformation. The reaction described here represents the first catalytic reaction that provides straightforward accesses toward both enantiomers of a broad range of valuable chiral hemiesters in high optical purity. It is important to note that most of these chiral hemiesters have been employed in the syntheses of various natural products and biologically important compounds.[1–8] The availability of the catalyst, the simple experimental procedure and the easy yet quantitative recovery of the catalyst renders this reaction a highly attractive synthetic method. Studies aiming to expand the synthetic utility of the reaction and to gain mechanistic insights into the origin of highly selective catalysis are in progress.

References and Notes for Example 1

1. Toyota, M.; Yokota, M.; Ihara, M. *Organic Lett.* 1999, 1, 1627–1629.
2. Couche, E.; Deschatrettes, R.; Poumellec, K.; Bortolussi, M.; Mandvile, G.; Bloch, R. *Synlett.* 1999, 87–88.
3. Paterson, I.; Cowden, C. J.; Woodrow, M. D. *Tetrahedron Lett.* 1998, 39, 6037–6040.
4. a) Borzilleri, R. B.; Weinreb, S. M. *J. Am. Chem. Soc.* 1994, 116, 9789–9790. b) Borzilleri, R. B.; Weinreb, S. M.; Parvez, M. *J. Am. Chem. Soc.* 1995, 117, 10905–10913.
5. Marie, F. B. C.; Mackiewicz, P.; Roul, J. M.; Buendia, *J. Tetrahedron Lett.* 1992, 33, 4889–4892.
6. a) Ohtani, M.; Matsuura, T.; Watanabe, F.; Narisada, M. *J. Org. Chem.* 1991, 56, 4120–4123. b) Ohtani, M.; Matsuura, T.; Watanabe, F.; Narisada, M. *J. Org. Chem.* 1991, 56, 2122–2127.
7. Wender, P. A.; Singh, S. K. *Tetrahedron Lett.* 1990, 31, 2517–1520.
8. Suzuki, T.; Tomino, A.; Matsuda, Y.; Unno, K.; Kametani, T. *Heterocycles,* 1980, 14, 1735–1738.
9. a) Heathcock, C. H.; Hadley, C. R.; Rosen, T.; Theisen, P. D.; Hecker, S. J. *J. Med. Chem.* 1987, 30, 1858–1873. b) Hecker, S. J.; Heathcock, C. H. *J. Am. Chem. Soc.* 1986, 108, 4586–4594. c) Rosen, T.; Heathcock, C. H. *J. Am. Chem. Soc.* 1985, 107, 3731–3733.
10. For representative examples of chiral auxiliary-based methods see: a) Albers, T.; Biagini, S. C. G.; Hibbs, D. E.; Hursthouse, M. B.; Malik, K. M. A.; North, M.; Uriarte, E.; Zagotto, G. *Synthesis* 1996, 393–398. b) Konoike, T.; Araki, Y. *J. Org. Chem.* 1994, 59, 7849–7854. c) Shimizu, M.; Matsukawa, K.; Fujisawa, T. *Bull. Chem. Soc. Jpn.* 1993, 66, 2128–2130. d) Theisen, P. D.; Heathcock, C. H. *J. Org. Chem.* 1993, 58, 142–146.
11. For most successful examples of chiral mediator-based methods see: a) Seebach, D.; Jaeschke, G.; Wang, Y. M. *Angew. Chem. Int. Ed. Engl.* 1995, 34, 2395–2396. b) Jaeschke, G.; Seebach, D. *J. Org. Chem.* 1998, 63, 1190–1197. c) Bolm, C.; Gerlach, A.; Dinter, C. L. *Synlett.* 1999, 195–196.
12. a) Hiratake, J.; Yamamoto, Y.; Oada, J. *J. Chem. Soc. Chem. Commun.* 1985, 1717–1719. b) Hiratake, J.; Inagaki, M.; Yamamoto, Y.; Oada, J. *J. Chem. Soc. Perkin. Trans. I* 1987, 1053–1058.
13. a) Aitken, R. A.; Gopal, J.; Hirst, J. A. *J. Chem. Soc. Chem. Commun.* 1988, 632–634. b) Aitken, R. A.; Gopal, J. *Tetrahedron: Asymmetry* 1990, 1, 517–520.
14. Ozegowski, R.; Kunath, A.; Schick, H. *Tetrahedron: Asymmetry* 1995, 6, 1191–1194.
15. a) Yamamoto, K.; Nishioka, T.; Oada, *J. Tetrahedra Lett.* 1988, 29, 1717–1720. b) Yamamoto, K.; Yamamoto, K.; Nishioka, T.; Oada, J. *Agric. Biol. Chem.* 1988, 52, 307–3092.
16. Pluim, H. Ph.D. Thesis, University of Groningen, Groningen, The Netherlands, 1982.
17. These modified cinchona alkaloids were first reported by Sharpless and coworkers as highly effective ligands for asymmetric dihydroxylations of alkenes. For leading references, see: a) Sharpless, K. B.; Amberg, W.; Bennani, Y, L.; Crispino, G. A.; Hartung, J.; Jeong, K.-S.; Kwong, H.-L.; Morikawa, K.; Wang, Z. -M.; Xu, D.; Zhang, X.-L. *J. Org. Chem.* 1992, 57, 2768. b) Crispino, G. A.; Jeong, K.-S.; Hartmuth, C. K.; Wang, Z.-M.; Xu, D.; Sharpless, K. B. *J. Org. Chem.* 1993, 58, 3785. c) Becker, H.; Sharpless, K. B. *Angew. Chem., Int. Ed. Engl.* 1996, 35, 451–454. d) Sharpless, K. B.; Amberg, W.; Bennani, Y, L.; Crispino, G. A.; Hartung, J.; Jeong, K.-S.; Kwong, H.-L.; Morikawa, K.; Wang, Z.-M.; Xu, D.; Zhang, X.-L. *J. Org. Chem.* 1991,56, 4585. e) Hartmuth, C. K.; VanNieuwenhze, M. S.; Sharpless, K. B. *Chem. Rev.* 1994, 94, 2483–2547.

Example 2

General Method for Synthesizing Tertiary Amine Catalysts

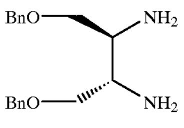

+

1

-continued

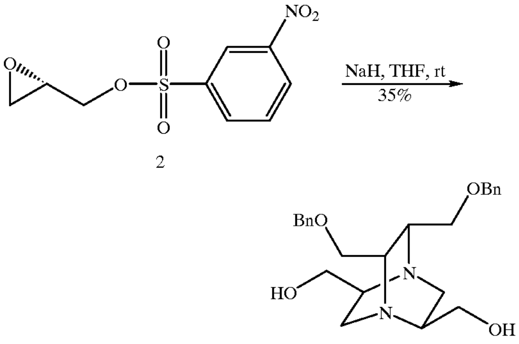

2

3

To a solution of diamine 1 (1.40 g, 4.67 mmol) in dry tetrahydrofiran (93 mL) under nitrogen at room temperature was added sodium hydride (60% suspension in mineral oil, 1.87 g, 46.7 mmol). The mixture was stirred for 10 minutes, and then glycidol nosylate 2 was added. After being stirred for 88 hours, the mixture was filtered, and the filtrate was concentrated under reduced pressure. The resulting residue was purified by chromatography [basic aluminum oxide, $CH_3OH:CH_2Cl_2$ (1:100 to 1:20)] to give the chiral tertiary amine 3 (667 mg, 35%) as a solid.

Example 3

Catalytic Desymmetrization of a Meso Bicyclic Succinic Anhydride Comprising a Urea

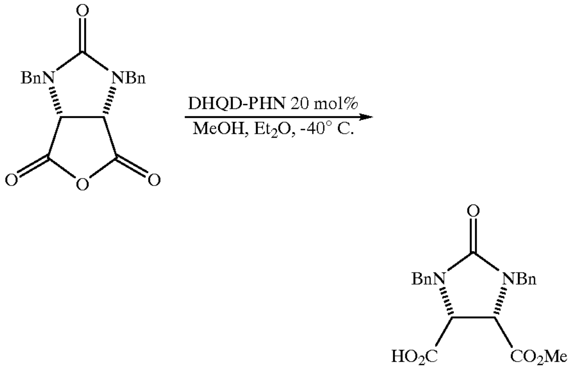

91% yield
93% ee

To a mixture of anhydride (16.8 mg, 0.05 mmol) and DHQD-PHN (20 mol %, 5 mg) in $Et_2O$ (2.5 mL) at −40° C., anhydrous MeOH (0.5 mmol, 20.2 ul) cooled at −20° C. was added in one portion. The resulting mixture was stirred until the reaction was complete (~30 hrs) as monitored by TLC (20% MeOH in $CH_2Cl_2$). The reaction was quenched with aqueous HCl (1 N, 3 mL). The aqueous layer was extracted with EtOAc (2×10 mL). The combined organic layer was dried over $MgSO_4$ and concentrated. The residue was purified by flash chromatography (100% $CH_2Cl_2$ to 10% MeOH in $CH_2Cl_2$) to afford the hemiester (16.7 mg, 91% yield). The ee of the hemiester was determined to be 93% by converting the hemiester into the corresponding ester amide (*J. Chem. Soc. Perkin. Trans I* 1987, 1053) via a reaction of the hemiester with (R)-1-(1-napthyl) ethyl amine. The ester amide was analyzed by chiral HPLC (Chiralpak, OD, 280 nm, 0.6 mL/min; retention times for the relevant diastereomers are 20.030 and 25.312 minutes, respectively).

Example 4

Catalytic Desymmetrization of a Meso Bicyclic Succinic Anhydride Comprising a Ketone

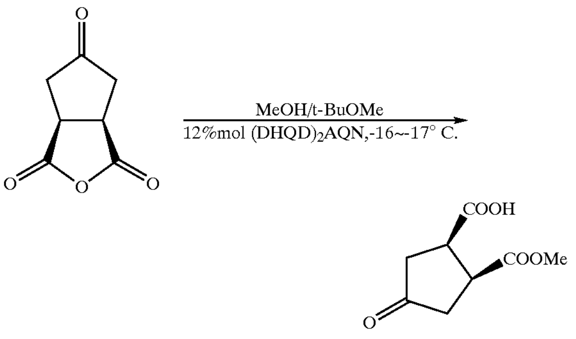

93% conversion
84% ee

Dry methanol (32 mg, 1.0 mmol) was added dropwise to a stirred solution of the anhydride (0.1 mol, 15.4 mg) and $(DHQD)_2AQN$ (12% mol, 10.3 mg) in t-butyl methyl ether at −16~−17° C. The reaction mixture was stirred at that temperature for 80 hrs. The reaction was then quenched with HCl (1 N, 3 mL). The aqueous phase was extracted with EtOAc (2×15 mL). The organic phase was combined, dried over $Na_2SO_4$, and the solvent was removed under reduced pressure. The ee of the hemiester was determined to be 84% by converting the hemiester into the corresponding ester amide (*J. Chem. Soc. Perkin. Trans I* 1987, 1053) via a reaction of the hemiester with (R)-1-(1-napthyl) ethyl amine. It was analyzed by HPLC (Hypersil SI 4.6×200 mm, 280 nm, 0.5 mL/min, Hexanes: i-Propanol=9:1; retention times for the relevant diastereomers are 28.040 and 33.479 minutes, respectively).

Incorporation by Reference

All of the patents and publications cited herein are hereby incorporated by reference.

Equivalents

Those skilled in the art will recognize, or be able to ascertain using no more than routine experimentation, many equivalents to the specific embodiments of the invention described herein. Such equivalents are intended to be encompassed by the following claims.

We claim:

1. A method of preparing a chiral, non-racemic dicarboxylic acid monoester from a prochiral cyclic anhydride, wherein said prochiral cyclic anhydride comprises at least two chiral centers, and an internal plane of symmetry or point of symmetry or both, comprising the step of:

reacting a prochiral cyclic anhydride, wherein said prochiral cyclic anhydride comprises at least two chiral centers, and an internal plane of symmetry or point of symmetry or both, with a primary alcohol in the presence of a chiral, non-racemic tertiary amine catalyst selected from the group consisting of $(DHQ)_2PHAL$, $(DHQD)_2PHAL$, $(DHQ)_2PYR$, $(DHQD)_2PYR$, $(DHQ)_2AQN$, $(DHQD)_2AQN$, DHQ-CLB, DHQD-CLB, DHQ-MEQ, DHQD-MEQ, DHQ-AQN, DHQD-AQN, DHQ-PHN, and DHQD-PHN, thereby producing a chiral, non-racemic dicarboxylic acid monoester.

2. The method of claim 1, wherein said prochiral cyclic anhydride is a substituted or unsubstituted succinic anhydride.

3. The method of claim 1, wherein said primary alcohol is methanol.

4. The method of claim 1, wherein said chiral, non-racemic tertiary amine catalyst is DHQD-PHN or $(DHQD)_2AQN$.

5. The method of claim 1, wherein said prochiral cyclic anhydride is a substituted or unsubstituted succinic anhydride; and said chiral, non-racemic tertiary amine catalyst is DHQD-PHN or $(DHQD)_2AQN$.

6. The method of claim 1, wherein said prochiral cyclic anhydride is a substituted or unsubstituted succinic anhydride; said primary alcohol is methanol; and said chiral, non-racemic tertiary amine catalyst is DHQD-PHN or $(DHQD)_2AQN$.

7. The method of claim 1, wherein said chiral, non-racemic tertiary amine catalyst is present in less than about 30 mol % relative to the prochiral cyclic anhydride.

8. The method of claim 1, wherein said chiral, non-racemic tertiary amine catalyst is present in less than about 20 mol % relative to the prochiral cyclic anhydride.

9. The method of claim 1, wherein said chiral, non-racemic tertiary amine catalyst is present in less than about 10 mol % relative to the prochiral cyclic anhydride.

10. The method of claim 1, wherein said chiral, non-racemic tertiary amine catalyst is present in less than about 5 mol % relative to the prochiral cyclic anhydride.

11. The method of claim 1, wherein said chiral, non-racemic dicarboxylic acid monoester has an enantiomeric excess greater than about 50%.

12. The method of claim 1, wherein said chiral, non-racemic dicarboxylic acid monoester has an enantiomeric excess greater than about 70%.

13. The method of claim 1, wherein said chiral, non-racemic dicarboxylic acid monoester has an enantiomeric excess greater than about 90%.

14. The method of claim 1, wherein said chiral, non-racemic dicarboxylic acid monoester has an enantiomeric excess greater than about 95%.

* * * * *

UNITED STATES PATENT AND TRADEMARK OFFICE

CERTIFICATE OF CORRECTION

PATENT NO. : 6,580,003 B2
APPLICATION NO. : 09/825167
DATED : June 17, 2003
INVENTOR(S) : Li Deng et al.

It is certified that error appears in the above-identified patent and that said Letters Patent is hereby corrected as shown below:

In the Specification

At Column 1, Line number 9, immediately before "BACKGROUND OF THE INVENTION," insert:
--GOVERNMENT SUPPORT
This invention was made with government support under R01 GM061591 awarded by the National Institutes of Health. The government has certain rights in the invention.--

Signed and Sealed this
Thirteenth Day of August, 2019

Andrei Iancu
*Director of the United States Patent and Trademark Office*